(12) United States Patent
Weaver et al.

(10) Patent No.: US 8,361,103 B2
(45) Date of Patent: Jan. 29, 2013

(54) LOW PROFILE IVC FILTER

(76) Inventors: Karla Weaver, Framingham, MA (US); Sally Thornton, Marlborough, MA (US)

(*) Notice: Subject to any disclaimer, the term of this patent is extended or adjusted under 35 U.S.C. 154(b) by 1618 days.

(21) Appl. No.: 10/361,063

(22) Filed: Feb. 7, 2003

(65) Prior Publication Data
US 2004/0158273 A1 Aug. 12, 2004

(51) Int. Cl.
*A61B 17/00* (2006.01)
(52) U.S. Cl. .................................................. 606/200
(58) Field of Classification Search ............. 606/200, 606/190–194, 198, 127, 128, 113, 114, 205–207, 606/108, 159; 128/899; 623/1.1, 1.11; 604/104–107
See application file for complete search history.

(56) References Cited

U.S. PATENT DOCUMENTS

| | | | | |
|---|---|---|---|---|
| 4,425,908 | A | * 1/1984 | Simon | 128/899 |
| 4,643,184 | A | * 2/1987 | Mobin-Uddin | 606/200 |
| 4,688,553 | A | 8/1987 | Metals | |
| 4,781,177 | A | 11/1988 | Lebigot | |
| 4,817,600 | A | 4/1989 | Herms et al. | |
| 4,957,501 | A | 9/1990 | Lahille et al. | |
| 4,969,891 | A | 11/1990 | Gewertz | |
| 4,990,156 | A | * 2/1991 | Lefebvre | 606/200 |
| 5,059,205 | A | * 10/1991 | El-Nounou et al. | 606/200 |
| 5,071,407 | A | 12/1991 | Termin et al. | |
| 5,108,418 | A | 4/1992 | Lefebvre | |
| 5,133,733 | A | 7/1992 | Rasmussen et al. | |
| 5,152,777 | A | * 10/1992 | Goldberg et al. | 606/200 |
| 5,160,342 | A | 11/1992 | Reger et al. | |
| 5,221,261 | A | 6/1993 | Termin et al. | |
| 5,300,086 | A | 4/1994 | Gory et al. | |
| 5,324,304 | A | * 6/1994 | Rasmussen | 606/200 |
| 5,329,942 | A | 7/1994 | Gunther et al. | |
| 5,344,427 | A | 9/1994 | Cottenceau et al. | |
| 5,370,657 | A | 12/1994 | Irie | |
| 5,549,626 | A | 8/1996 | Miller et al. | |
| 5,776,162 | A | 7/1998 | Kleshinski | |
| 5,827,324 | A | 10/1998 | Cassell et al. | |
| 5,836,969 | A | 11/1998 | Kim et al. | |
| 5,893,869 | A | 4/1999 | Barnhart et al. | |
| 6,126,673 | A | 10/2000 | Kim et al. | |
| 6,168,579 | B1 | 1/2001 | Tsugita | |
| 6,171,328 | B1 | 1/2001 | Addis | |

(Continued)

FOREIGN PATENT DOCUMENTS

| | | | |
|---|---|---|---|
| DE | 3429850 | * | 2/1986 |
| EP | 0 350 043 A1 | | 1/1990 |

(Continued)

OTHER PUBLICATIONS

Roettgering, Guenter; trnalstion of patent DE3429850, Feb. 1986.*

*Primary Examiner* — Elizabeth Houston
(74) *Attorney, Agent, or Firm* — Seager, Tufte & Wickhem LLC

(57) ABSTRACT

Intravascular filtering devices for placement within a blood vessel are disclosed. An intravascular filter in accordance with the present invention may include a plurality of elongated filter legs biased to radially expand from a collapsed position to a conical-shaped position when deployed in a blood vessel. Each of the filter legs may include a hook region configured to engage the vessel wall. The filter legs may vary in length and/or cross-sectional diameter. In certain embodiments, the dimensions and/or orientation of the hook regions can be configured to allow the filter device to be collapsed into a relatively small introducer catheter or sheath.

13 Claims, 4 Drawing Sheets

U.S. PATENT DOCUMENTS

| | | | |
|---|---|---|---|
| 6,179,859 B1 | 1/2001 | Bates et al. | |
| 6,193,739 B1 * | 2/2001 | Chevillon et al. | 606/200 |
| 6,217,600 B1 | 4/2001 | DiMatteo | |
| 6,231,589 B1 * | 5/2001 | Wessman et al. | 606/200 |
| 6,258,026 B1 * | 7/2001 | Ravenscroft et al. | 600/200 |
| 6,391,045 B1 | 5/2002 | Kim et al. | |
| 6,436,120 B1 | 8/2002 | Meglin | |
| 6,436,121 B1 | 8/2002 | Blom | |
| 6,443,971 B1 | 9/2002 | Boylan et al. | |
| 6,468,290 B1 * | 10/2002 | Weldon et al. | 606/200 |
| 6,482,222 B1 | 11/2002 | Bruckheimer et al. | |
| 6,485,501 B1 | 11/2002 | Green | |
| 6,491,698 B1 | 12/2002 | Bates et al. | |
| 6,511,496 B1 | 1/2003 | Huter et al. | |
| 6,511,503 B1 | 1/2003 | Burkett et al. | |
| 6,569,191 B1 * | 5/2003 | Hogan | 623/1.11 |
| 7,147,649 B2 * | 12/2006 | Thomas | 606/200 |
| 2001/0011181 A1 * | 8/2001 | DiMatteo | 606/200 |
| 2002/0138097 A1 * | 9/2002 | Ostrovsky et al. | 606/200 |
| 2002/0193828 A1 * | 12/2002 | Griffin et al. | 606/200 |
| 2003/0078605 A1 * | 4/2003 | Bashiri et al. | 606/159 |

FOREIGN PATENT DOCUMENTS

| | | |
|---|---|---|
| FR | 2 591 900 A1 | 6/1987 |
| FR | 2 672 487 A1 | 8/1992 |
| WO | WO 01/60442 A1 | 8/2001 |
| WO | WO 01/62184 A2 | 8/2001 |
| WO | WO 02/069845 A2 | 9/2002 |
| WO | WO 02/089869 A2 | 11/2002 |

* cited by examiner

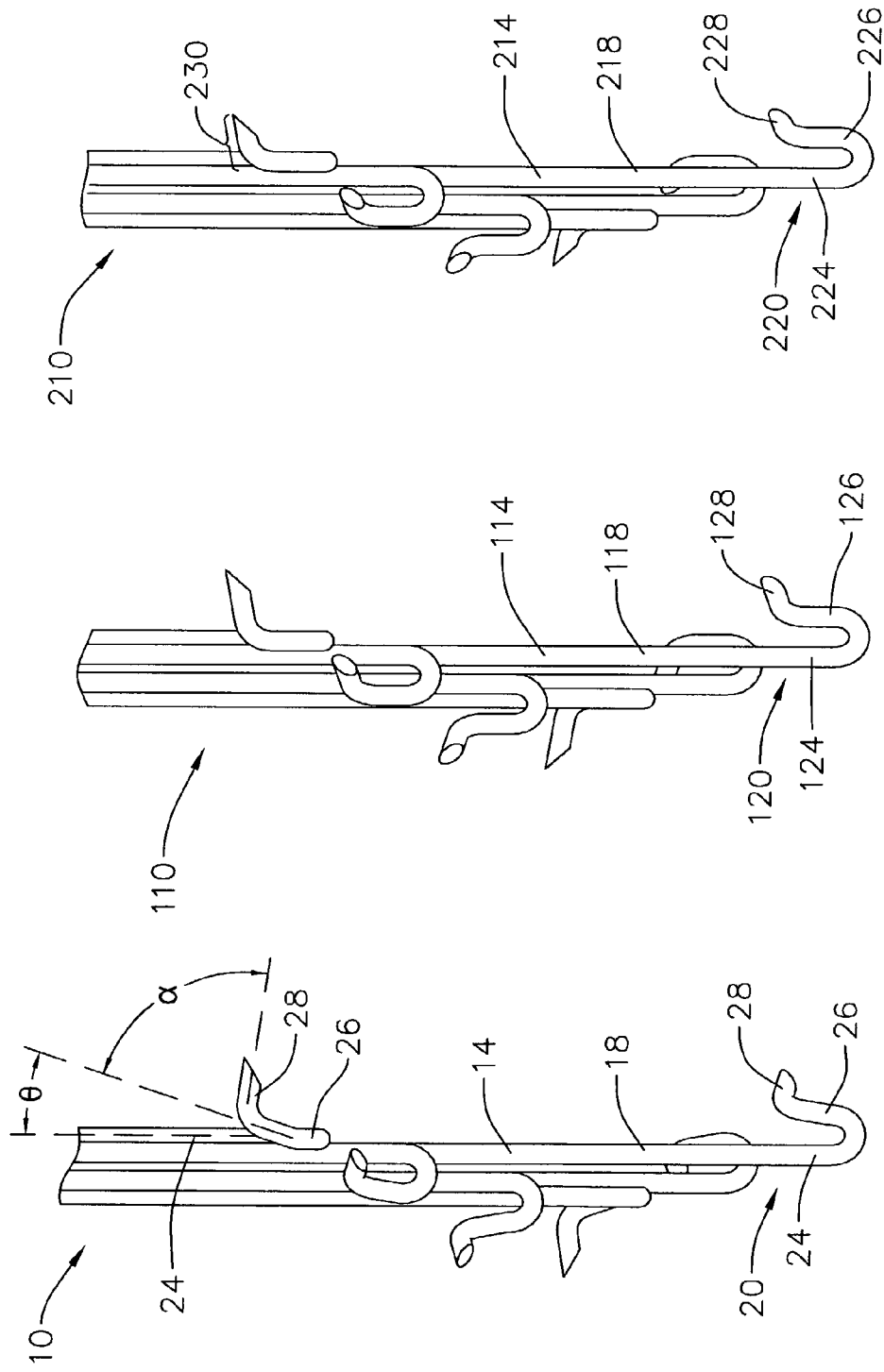

LOW PROFILE IVC FILTER

FIELD OF THE INVENTION

The present invention relates to devices for filtering blood clots within a vessel. More specifically, the present invention pertains to filters implantable within the vena cava.

BACKGROUND OF THE INVENTION

Vena cava filters are typically used in combination with other thrombolytic agents to treat pulmonary embolism within a patient. These devices are generally implanted within a vessel such as the inferior vena cava, and function by capturing blood clots (emboli) contained in the blood stream before they can reach the lungs and cause permanent damage to the patient. To trap emboli contained within the blood, many conventional vena cava filters utilize a plurality of elongated filter legs that can be expanded within the body to form a conical-shaped surface that captures blood clots without disturbing the flow of blood. Once collected, a natural clot lysing process occurs within the body to dissolve the blood clots collected by the filter.

Delivery of the vena cava filter within the body is generally accomplished via an introducer catheter or sheath percutaneously inserted through the femoral (groin) or jugular (neck) veins. Such introducer catheters or sheaths are generally tubular in shape, and include an inner lumen configured to transport the filter in a collapsed position through the body. Once transported to a desired location in the body (e.g. the inferior vena cava), the filter can then be removed from within the catheter or sheath, allowing the filter legs to spring open and engage the vessel wall. A hook, barb or other piercing means disposed on the base of each filter leg can be used to secure the filter to the vessel wall.

SUMMARY OF THE INVENTION

The present invention relates generally to devices for filtering blood clots within a vessel. In an exemplary embodiment of the present invention, an intravascular filter may comprise a plurality of elongated filter leg biased to radially expand from a collapsed position to a conical-shaped position when deployed in the blood vessel. Each filter leg may be attached proximally to an apical head, and may include one or more zigzag regions along their length to increase to clot capturability of the filter. A hook region on the distal section of each filter leg may be configured to pierce the vessel wall to secure the filter within the blood vessel.

According to one aspect of the present invention, one or more of the filter legs may vary in length such that the hook regions on the differing filter legs are longitudinally offset from each other. The length of each filter leg may vary individually, or may be arranged in opposing sets wherein each set of filter legs is longitudinally offset from each other. In certain embodiments, the cross-sectional diameter of one or more of the filter legs may be reduced. The variable length and/or the reduced cross-sectional diameter of the filter legs reduces the overall profile of the filter, allowing the device to be inserted into a relatively small introducer catheter or sheath.

The hook region on each filter leg may comprise a main section, a reversibly bent section, and a pointed tip section. The reversibly bent section may be bent through an angle of about 180° in the plane tangential to the conical configuration of the filter leg and contiguous to the main section. The reversibly bent section may be disposed at an angle relative to the main section, or in the alternative, may be disposed parallel to the main section. The pointed tip section of the hook region extends at an angle from the reversibly bent section and is oriented in a direction towards the vessel wall.

BRIEF DESCRIPTION OF THE DRAWINGS

FIG. 3 is a perspective view of the intravascular filter of FIG. 1, showing the distal section of the filter legs in a collapsed position;

FIG. 4 is a perspective view of the distal portion of an intravascular filter in accordance with an alternative embodiment of the present invention, wherein the filter includes longitudinally offset hooks with no hook bend;

FIG. 5 is a perspective view of the distal portion of an intravascular filter in accordance with an alternative embodiment of the present invention, wherein the filter includes longitudinally offset hooks with no hook bend and a reduced height;

DETAILED DESCRIPTION OF THE INVENTION

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials are illustrated for the various elements, those skilled in the art will recognize that many of the examples provided have suitable alternatives that may be utilized.

Figure 1:
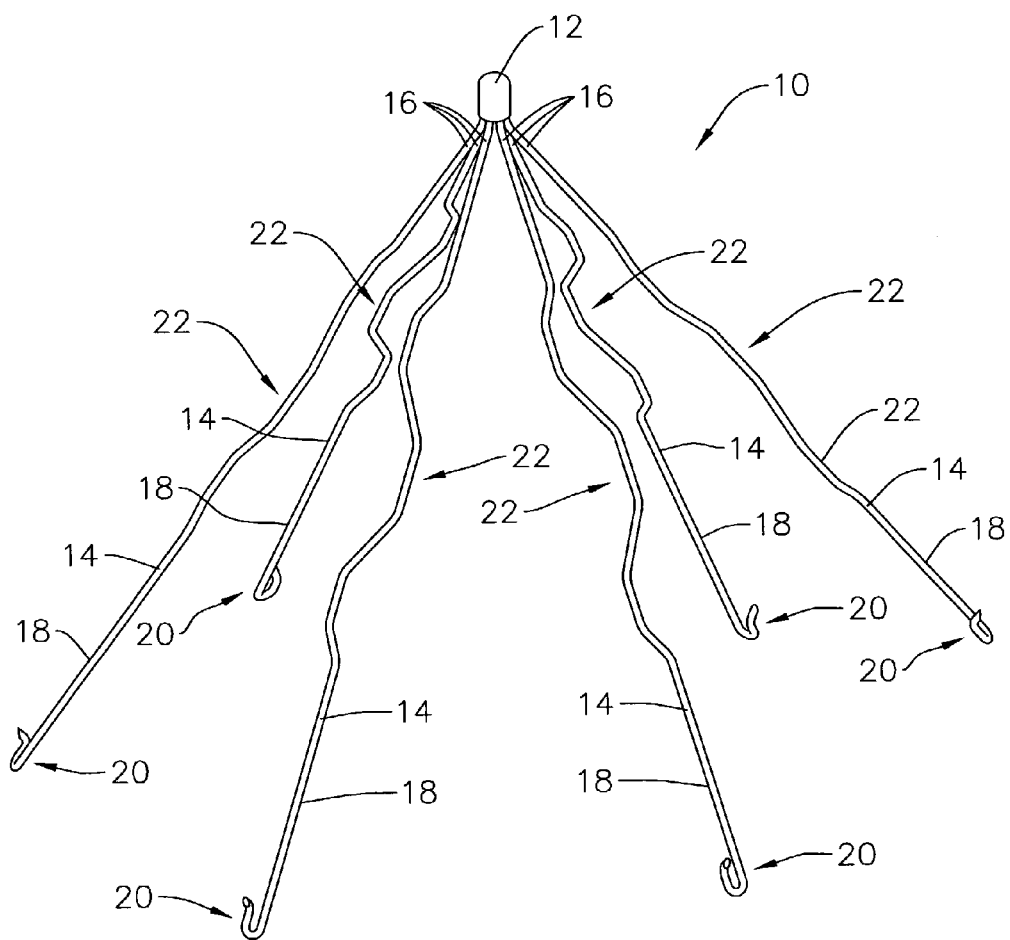
FIG. 1 is a perspective view of the an intravascular filter in accordance with an exemplary embodiment of the present invention.

FIG. 1 is a perspective view of an intravascular filter 10 in accordance with an exemplary embodiment of the present invention. Intravascular filter 10 comprises an apical head 12, and a plurality of elongated filter legs 14 each having a proximal section 16 and a distal section 18. Each of the filter legs 14 are biased to radially expand from a substantially straight position when collapsed within an introducer catheter or sheath to an outswept, conical-shaped position when deployed in the blood vessel. A hook region 20 on the distal section 18 of each filter leg 14 is configured to pierce the vessel wall to secure the filter 10 within the blood vessel.

The filter legs 14 may be formed from a metal or metal alloy such as titanium, platinum, tantalum, tungsten, stainless steel (e.g. type 304 or 316) or cobalt-chrome alloy. The filter legs 14 may include an anti-thrombogenic coating such as herapin (or its derivatives), urokinase, or PPack (dextrophenylalanine proline arginine chloromethylketone) to prevent insertion site thrombosis. In certain embodiments, the filter legs 14 may be formed from a shape-memory material such as nickel-titanium alloy (Nitinol). A slight outward bend can be imparted to each filter leg 14 by heating the alloy beyond its final austenitic temperature, and then bending the filter leg 14 to a pre-defined shape. The filter legs 14 can be configured to revert to their pre-defined (i.e. bent) shape at or near body temperature (37° C.), allowing each individual filter leg 14 to maintain a straight position until deployed in the vessel.

The length of each filter leg 14 may vary such that the hook regions 20 on the various filter legs 14 are longitudinally offset from each other. As shown in FIG. 1, for example, filter 10 may include six independent filter legs each of differing length. The respective lengths of each filter leg 14 can be selected such that, when the filter 10 is radially collapsed and loaded into the introducer catheter or sheath, the hook regions 20 on each filter leg 14 are spaced apart from each other. This staggered arrangement reduces the overall profile of the filter 10, and reduces the likelihood that the hook regions 20 on each filter leg 14 will interfere with each other when the filter 10 is radially expanded within the vessel.

One or more zigzag regions 22 disposed along the length of each leg 14 may be employed to increase the total surface area of the filter 10, and to impart flexibility to the filter legs 14. The size and shape of the one or more zigzag regions 22 can be selected to impart a particular degree of clot capturability within the vessel while maintaining the flow of blood through the filter 10. In those embodiments employing a shape-memory material, the zigzag regions 22 can be configured to revert from a straight shape to the zigzag shape when deployed in the vessel, further reducing the profile of the filter legs 14 during delivery.

Figure 2:
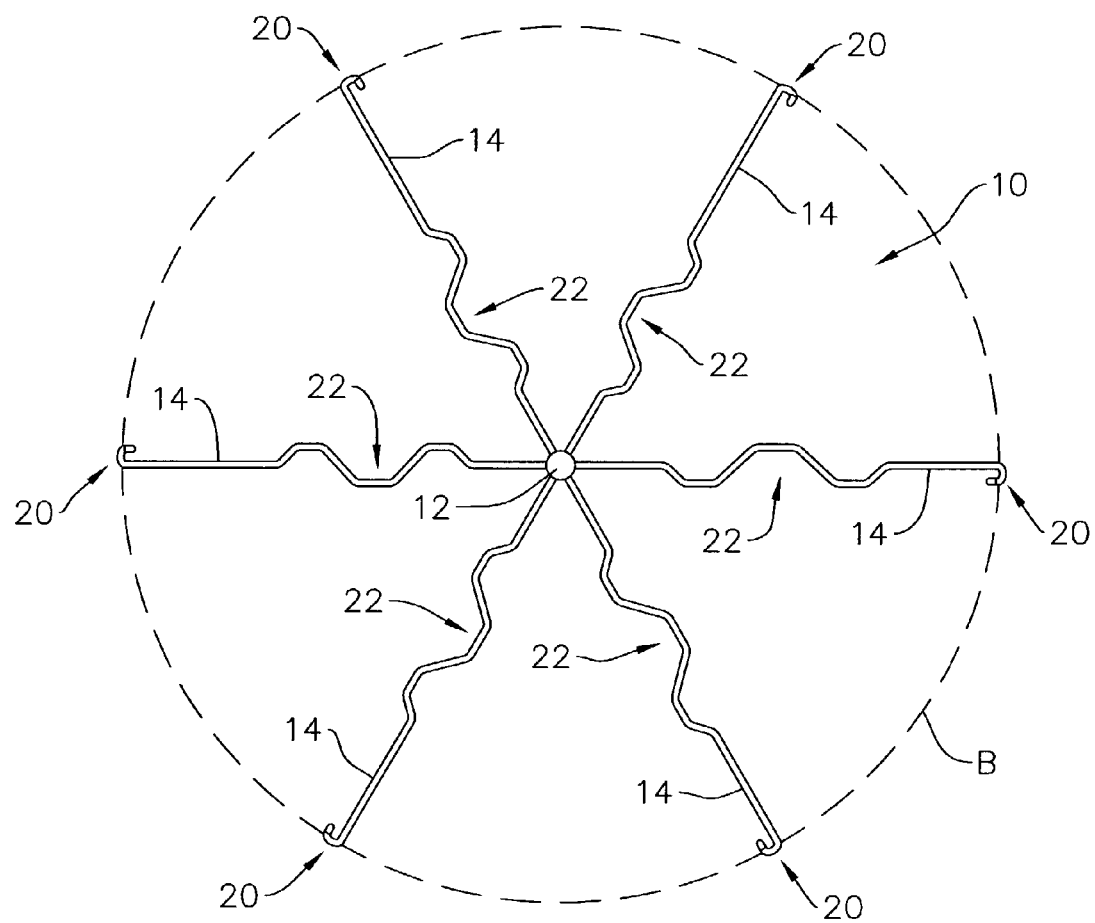
FIG. 2 is a top perspective view of the intravascular filter of FIG. 1.

FIG. 2 is a top perspective view of filter 10, showing the arrangement of the filter legs 14 about the apical head 12. As shown in FIG. 2, the filter legs 14 diverge at various angles from the apical head 12 such that the hook region 20 on each filter leg 14 engages the vessel wall at approximately the same longitudinal location within the vessel, indicated by base B. The filter legs 14 can be disposed circumferentially at equidistant (i.e. 60°) intervals with respect to each other such that the filter 10 symmetrically engages the vessel wall.

FIG. 3 is a perspective view showing the distal portion of the filter legs 14 in a radially collapsed position prior to being loaded into the introducer catheter or sheath. As shown in FIG. 3, each of the filter legs 14 may vary in length such that the hook regions 20 are longitudinally offset from each other when the filter 10 is in the collapsed position.

The hook region 20 of each filter leg 14 includes a main section 24, a reversibly bent section 26, and a pointed tip section 28. The reversibly bent section 26 is bent through an angle of about 180° in the plane tangential to the conical configuration of the filter leg 14, and is disposed contiguous to the main section 24, forming a landing pad that prevents the pointed tip section 28 from distending the wall of the vessel. In the exemplary embodiment illustrated in FIG. 3, the reversibly bent section 26 bends at an angle θ relative to the main section 24.

The pointed tip section 28 is bent at an angle a relative to the reversibly bent section 26, thus orienting the pointed tip section 28 in a direction towards the vessel wall. The pointed tip section 28 of hook region 20 is configured to pierce the vessel wall, but is prevented from distending the wall of the vessel via the reversibly bent section 26.

The profile of the filter in the collapsed position may be in the range of 5 Fr. to 12 Fr., and more specifically, 5 Fr. to 9 Fr., depending on the dimensions and orientation of the filter legs and hook regions. In certain embodiments employing several of the features described herein, the profile of the filter in the collapsed position may be 5 or 6 Fr., allowing the device to be inserted into a smaller introducer catheter or sheath. The reduction in the overall profile of the filter may, under certain conditions, permit the filter to be inserted into the body at different locations other than through the femoral or jugular veins (e.g. the antecubital region) of the patient.

FIG. 4 is a perspective view of the distal portion of an intravascular filter 110 in accordance with an alternative embodiment of the present invention. As shown in FIG. 4, hook region 120 comprises a main section 124, a reversibly bent section 126, and a pointed tip section 128. In the exemplary embodiment shown in FIG. 4, the reversibly bent section 126 is bent through an angle of about 180° in the plane tangential to the conical configuration of the filter leg 114, and is disposed parallel (i.e. θ=0°) and contiguous to the main section 124. The pointed tip section 128 of the hook region 120 is bent at an angle relative to the reversibly bent section 126, orienting the pointed tip section 28 in a direction towards the vessel wall. In use, the parallel configuration of the reversibly bent section 126 with the main section 125 reduces the overall profile of the filter 10, allowing the use of a smaller introducer catheter or sheath.

FIG. 5 is a perspective view of the distal portion of an intravascular filter 210 in accordance with an alternative embodiment of the present invention, wherein the filter 210 includes longitudinally offset hooks with no hook bend and a reduced height. As shown in FIG. 5, hook region 220 comprises a main section 224, a reversibly bent section 226 bent through an angle of about 180° in the plane tangential to the conical configuration of the filter leg 214 and disposed parallel and contiguous to the main section 224, and a pointed tip section 228 that is bent at an angle relative to the reversibly bent section 226 and oriented in a direction towards the vessel wall.

In the exemplary embodiment illustrated in FIG. 5, the pointed tip section 228 of each filter leg 214 has a reduced height, indicated generally by bracket 230. The reduction in height of the pointed tip section 228 further reduces the overall profile of the filter 210, allowing the device to be loaded into a smaller introducer catheter or sheath.

Figure 6:
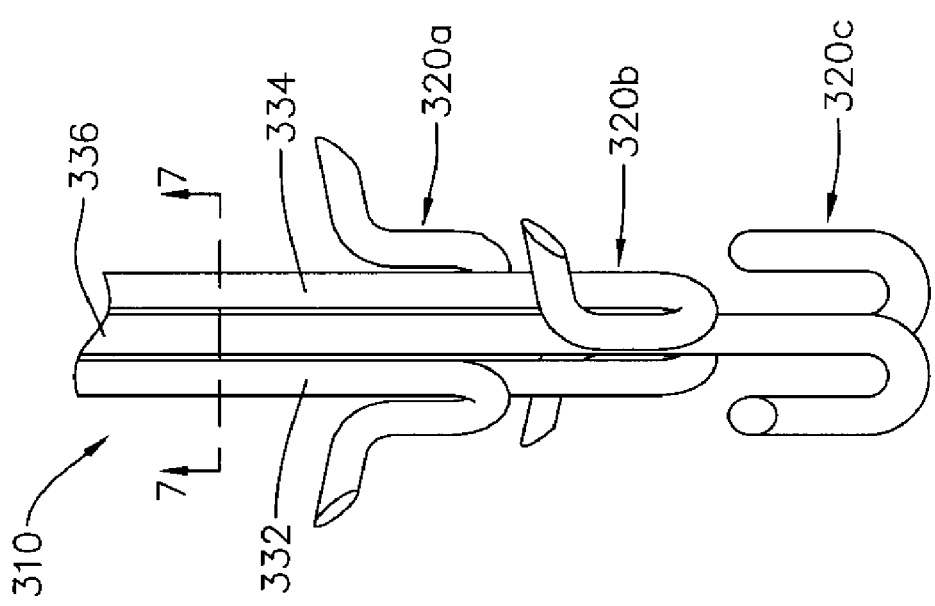
FIG. 6 is a perspective view of the distal portion of an intravascular filter in accordance with an alternative embodiment of the present invention, wherein the filter includes longitudinally offset sets of opposing filter legs.

FIG. 6 is a perspective view showing the distal portion of an intravascular filter 310 in accordance with an alternative embodiment of the present invention, wherein the filter legs are arranged in opposing sets, each set spaced longitudinally from each other. As shown in FIG. 6, intravascular filter 310 comprises a first set 332 of filter legs, a second set of filter legs 334 of greater length than the first set of filter legs 332, and third set of filter legs 336 of greater length than second set of filter legs 334. Each set of filter legs 332, 334, 336 includes a hook region 320 having a main section 322, a reversibly bent section 324 bent through an angle of about 180° in the plane tangential to the conical configuration of the filter leg 314 and disposed parallel and contiguous to the main section 324, and a pointed tip section 326 bent at an angle relative to the reversibly bent section 326.

Each set of filter legs 332, 334, 336 may include a pair of opposing filter legs that are configured to radially expand in opposing fashion within the vessel. The first, second, and third sets of filter legs 332, 334, 336 each differ in length such that the hook regions 320a, 320b, 320c on each set of filter legs 332, 334, 336 are longitudinally spaced apart from each other, thus providing a staggered arrangement that reduces the profile of the filter 310 when collapsed, and reduces the likelihood that the hook regions 220a, 220b, 220c on each filter leg 214 will interfere with each other when radially expanded.

Figure 7:
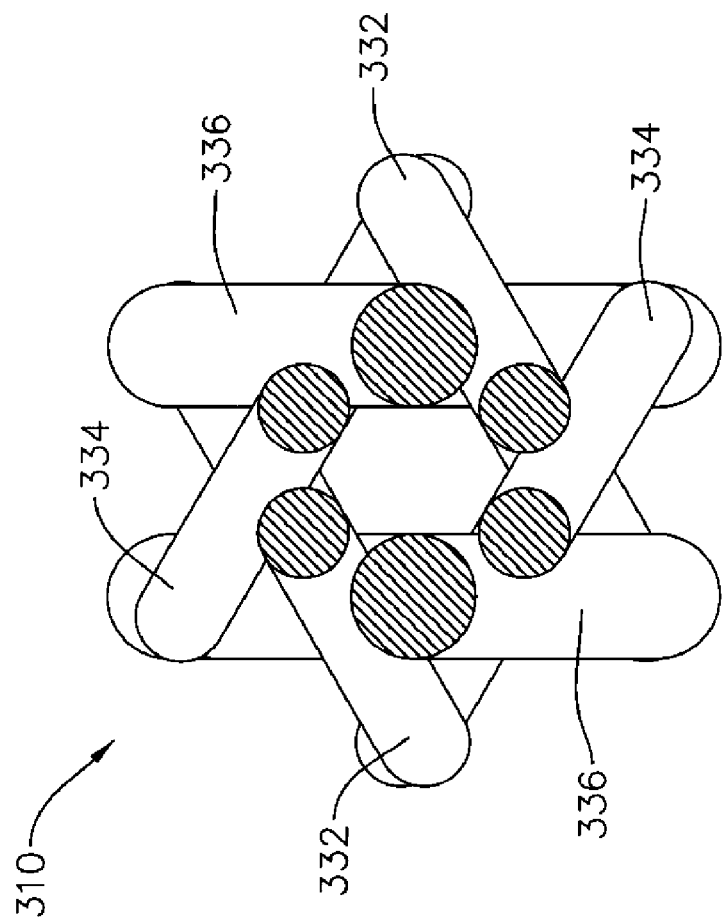
FIG. 7 is a perspective view of the intravascular filter of FIG. 6 along line 7-7, showing the cross-sectional diameter of the filter legs.

FIG. 7 is a view of intravascular filter 310 along line 7-7, showing the cross-sectional diameter of each set of filter legs 332, 334, 336. As shown in FIG. 7, the diameter of the third (i.e. longest) set of filter legs 336 may have a cross-sectional diameter greater than the cross-sectional diameter of the first and second set of filter legs 332, 334, which are reduced in diameter. In certain embodiments, for example, the diameter of the third set of filter legs 336 may be about 0.018 inches, whereas the diameter of the first and second set of filter legs 332, 334 may be about 0.016 inches.

The amount of radial force each set of filter legs 332, 334, 336 exerts on the wall of the vessel is dependent on several factors, including the diameter of the wire, and the nominal (i.e. static) base diameter of the filter 310. To compensate for the reduction of diameter of the first and second set of filter legs 332, 334, the overall base diameter of the filter 310 may be increased. In certain embodiments, for example, the base diameter of the filter can be increased from 38.5 mm to 55 mm to enable ligation within a vessel having a size in the range of 14 mm to 28 mm. It should be understood, however, that the necessary expansion in the base diameter is dependent on many factors, including the dimensions and composition of the filter legs, and the size of the vessel.

Having thus described the several embodiments of the present invention, those of skill in the art will readily appreciate that other embodiments may be made and used which fall within the scope of the claims attached hereto. Numerous advantages of the invention covered by this document have been set forth in the foregoing description. It will be understood that this disclosure is, in many respects, only illustrative. Changes may be made in details, particularly in matters of shape, size and arrangement of parts without exceeding the scope of the invention.

What is claimed is:

1. An intravascular filter device for placement within a blood vessel, comprising:
    a plurality of elongated filter legs each having a proximal section, a distal section, and a length, the distal section of each elongated filter leg including a hook region configured to engage the wall of the blood vessel;
    wherein the plurality of elongated filter legs include a first pair of filter legs having a first length, a second pair of filter legs having a second length greater than the first length, and a third pair of filter legs having a third length that is greater than the second length; and
    wherein the first pair of filter legs has a cross-sectional diameter along the majority of its length, the second pair of filter legs has a cross-sectional diameter along a majority of its length and the third pair of filter legs has a cross-sectional diameter along a majority of its length, wherein the cross-sectional diameter of the third pair of filter legs is greater than the cross-sectional diameter of the first pair of filter legs and the second pair of filter legs.

2. The intravascular filter device of claim 1, wherein said plurality of filter legs are biased to radially expand from a collapsed position to an expanded position when deployed in the blood vessel.

3. The intravascular filter device of claim 2, wherein the profile of the intravascular filter in the collapsed position is between 5-12 Fr.

4. The intravascular filter device of claim 2, wherein the profile of the intravascular filter in the collapsed position is 6 Fr.

5. The intravascular filter device of claim 2, wherein the profile of the intravascular filter in the collapsed position is 5 Fr.

6. The intravascular filter device of claim 1, wherein said filter legs are formed of a metal.

7. The intravascular filter device of claim 6, wherein said metal is shape-memory metal.

8. The intravascular filter device of claim 1, wherein each filter leg includes a zigzag region.

9. The intravascular filter device of claim 1, wherein said hook region comprises a main section, a reversibly bent section, and a pointed tip section.

10. The intravascular filter device of claim 9, wherein said reversibly bent section is bent at an angle relative to the main section.

11. The intravascular filter device of claim 9, wherein said reversibly bent section is substantially parallel to the main section.

12. The intravascular filter device of claim 9, wherein said pointed tip section is bent at an angle relative to the reversibly bent section.

13. The intravascular filter device of claim 1, further comprising an apical head coupled to the proximal section of each of said plurality of elongated filter legs.

* * * * *

UNITED STATES PATENT AND TRADEMARK OFFICE
CERTIFICATE OF CORRECTION

PATENT NO. : 8,361,103 B2
APPLICATION NO. : 10/361063
DATED : January 29, 2013
INVENTOR(S) : Weaver et al.

It is certified that error appears in the above-identified patent and that said Letters Patent is hereby corrected as shown below:

In the Specifications

Column 3, Line 51: delete "a" and insert -- $\alpha$ --.

Signed and Sealed this
Seventh Day of January, 2014

Margaret A. Focarino
*Commissioner for Patents of the United States Patent and Trademark Office*